(12) United States Patent
Wong

(10) Patent No.: US 8,409,444 B2
(45) Date of Patent: Apr. 2, 2013

(54) ACID ZIRCONIUM PHOSPHATE AND ALKALINE HYDROUS ZIRCONIUM OXIDE MATERIALS FOR SORBENT DIALYSIS

(75) Inventor: Raymond June-Hin Wong, Norman, OK (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 648 days.

(21) Appl. No.: 12/554,404

(22) Filed: Sep. 4, 2009

(65) Prior Publication Data

US 2010/0078387 A1 Apr. 1, 2010

Related U.S. Application Data

(60) Provisional application No. 61/101,280, filed on Sep. 30, 2008.

(51) Int. Cl.
*B01D 15/36* (2006.01)
*B01D 61/26* (2006.01)
*B01D 61/28* (2006.01)
*B01D 27/00* (2006.01)
*B01D 24/00* (2006.01)
*B01D 24/10* (2006.01)
*B01D 37/00* (2006.01)
*B01D 39/00* (2006.01)
*B01J 20/04* (2006.01)

(52) U.S. Cl. ........ 210/660; 210/483; 210/488; 210/489; 210/490; 210/501; 210/502.1; 210/503; 210/644; 210/645; 210/647; 210/679; 210/681; 502/400; 502/416

(58) Field of Classification Search ............... 210/198.2, 210/483, 488, 489, 490, 501, 502.1, 503, 210/644, 645, 647, 660, 679, 681; 502/400, 502/416
See application file for complete search history.

(56) References Cited

U.S. PATENT DOCUMENTS

| | | |
|---|---|---|
| 6,627,164 B1 | 9/2003 | Wong |
| 6,818,196 B2 | 11/2004 | Wong |
| 6,878,283 B2 | 4/2005 | Thompson |
| 7,033,498 B2 | 4/2006 | Wong |
| 2006/0140840 A1 | 6/2006 | Wong |

FOREIGN PATENT DOCUMENTS

WO 03041764 A1 5/2003

OTHER PUBLICATIONS

Cobe Renal Care, Inc., "Guide to Custom Dialysis," Product No. 306100-005, Revision E, Sep. 1993, pp. 1-52 (54 pages).
Cobe Renal Care, Inc., "Sorbent Dialysis Primer," Product No. 306100-006, Edition 4, Sep. 1993, pp. 1-46 (56 pages).
Extended European Search Report issued in corresponding European Patent Application No. 09170378.5 dated Dec. 6, 2010 (7 pages).

*Primary Examiner* — John Kim
(74) *Attorney, Agent, or Firm* — Kilyk & Bowersox, P.L.L.C.

(57) ABSTRACT

A combination of acid zirconium phosphate and alkaline hydrous zirconium oxide are utilized as ion-exchange materials, for example, in sorbent dialysis. The combination provides for dialysate regeneration while maintaining constant and controlled levels of $Na^+$, $HCO_3^-$, and pH.

29 Claims, 6 Drawing Sheets

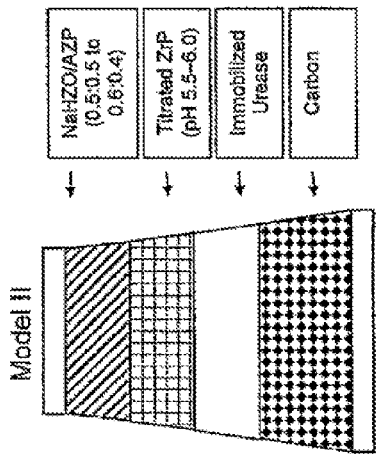
FIG. 1A
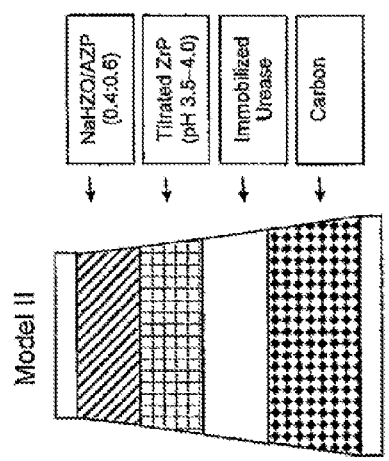
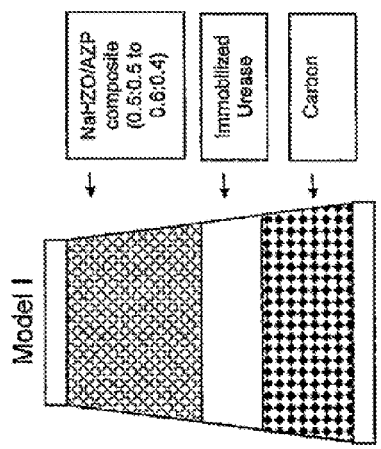
FIG. 1B
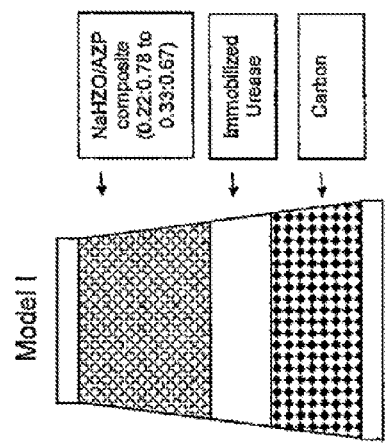

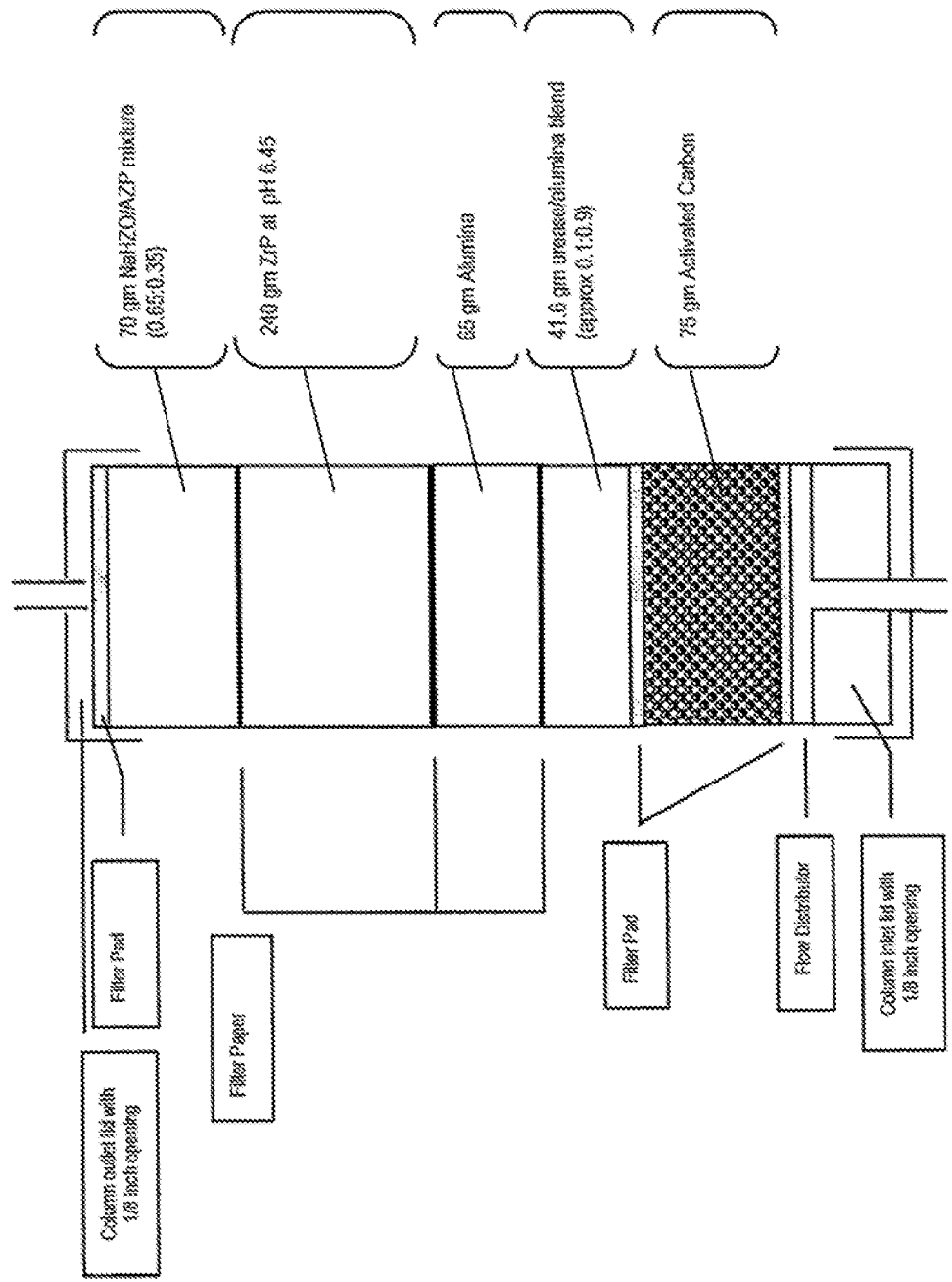

ACID ZIRCONIUM PHOSPHATE AND ALKALINE HYDROUS ZIRCONIUM OXIDE MATERIALS FOR SORBENT DIALYSIS

This application claims the benefit under 35 U.S.C. §119 (e) of prior U.S. Provisional Patent Application No. 61/101,280, filed Sep. 30, 2008, which is incorporated in its entirety by reference herein.

FIELD OF THE INVENTION

The present invention relates to ion-exchange materials and in particular, to acid zirconium phosphate materials and alkaline hydrous zirconium oxide materials that are useful, for example, in sorbent dialysis.

BACKGROUND OF THE INVENTION

Single-pass and sorbent dialysis systems both provide treatment for patients with acute or chronic kidney disease. Both systems deliver dialysate to the dialyzer in prescribed amounts to cleanse the blood of impurities, correct the patient's body chemistry, and remove excess fluid. Sorbent dialysis differs from traditional single-pass dialysis in that sorbent systems use less water than single-pass machines and do not require special plumbing. Single-pass systems use approximately 120 liters of water during a typical 4-hour treatment. In single-pass dialysis, a water treatment system is required to continuously pump purified water into the system to be blended with the bicarbonate and acid bath to create the final dialysate. This requires special plumbing to connect the single-pass machine to both the water treatment system and to a drain into which the used dialysate and rejected source water are disposed.

By utilizing sorbent technology, a dialysis system can provide highly-pure dialysate for 3- to 8-hour treatments using only 6 liters of potable tap water. The sorbent cartridge purifies the initial dialysate and continuously recirculates and regenerates the dialysate throughout the treatment. This not only eliminates the need to purchase and maintain an expensive water treatment system, but provides a high degree of transportability compared to conventional dialysis systems. Because sorbent systems do not require special wiring or plumbing, sorbent dialysis can be performed almost anywhere: in dialysis centers, hospital rooms, nursing homes, and home-care environments.

Sorbent systems provide a gentle way to achieve an electrolyte and chemical balance. Single-pass machines deliver a constant dialysate prescription to the patient. This forces the patient's body chemistry to change to match the dialysate prescription. This can cause some of the common side effects often associated with single-pass dialysis, such as nausea, cramping, and hypotension. During a sorbent dialysis treatment, urea is dismantled within the cartridge and combined with other solutes to replenish the sodium chloride and sodium bicarbonate required to correct the patient's body chemistry. Because the patient's body fluid volume is much larger than the dialysate volume, the patient is able to control the dialysate. The sorbent cartridge performs multiple tasks: it serves as a dialysate purification system, maintains dialysate pH balance, and binds uremic wastes.

Six liters of potable tap water and prescribed amounts of sodium chloride, sodium bicarbonate, and dextrose are used to create the initial dialysate solution. This mixture is then passed through the sorbent cartridge. As it flows through the cartridge, bacteria, pyrogens, endotoxins, metals, and organic solutes are removed from the initial dialysate. The purified dialysate is stored in the dialysate reservoir bag until it is circulated to the dialyzer. Once it leaves the dialyzer, the spent dialysate and the patient's ultrafiltrate fluid pass through the sorbent cartridge, where both are converted into partially regenerated dialysate, known as cartridge effluent. An infusate system adds calcium, carbon dioxide, magnesium, and potassium to form a fully regenerated dialysate, which then flows back into the dialysate reservoir bag, ready to be sent to the dialyzer.

Zirconium phosphate (ZrP) particles and hydrous zirconium oxide (HZO) particles are used as ion-exchange materials and are particularly useful as a sorbent material in regenerative kidney dialysis. Zirconium phosphate in the sodium or hydrogen form serves as a cation exchanger and absorbs cations such as ammonium ($NH_4^+$), calcium ($Ca^+$), potassium ($K^+$), and magnesium ($Mg^{2+}$). In exchange for absorbing these cations, ZrP releases two other cations, sodium ($Na^+$) and hydrogen ($H^+$). Hydrous zirconium oxide in the acetate form acts as an anion exchanger. Thus, it binds anions such as phosphate ($P^-$) and fluoride ($F^-$) and releases acetate ($CH_3COO^-$) in exchange. Hydrous zirconium oxide is also an excellent adsorbent for metals, such as iron, mercury, lead, and aluminum.

The sorbent cartridge containing ZrP and HZO ion-exchange materials has been historically used for the REDY (REgenerative DialYsis) system. The REDY sorbent cartridge consists of several layers through which used dialysate passes: i) a purification layer consisting of activated charcoal; ii) an enzyme layer consisting of urease; iii) a cation exchange layer consisting of ZrP; iv) an anion exchange layer consisting of HZO; and v) an adsorbent layer consisting again of activated carbon. During regenerative dialysis, the used dialysate moves up through the layers of the cartridge. The enzymatic urease converts urea into ammonium carbonate. The ammonia and ammonium ions are then removed by the zirconium phosphate in exchange for $H^+$ and $Na^+$ ions. The carbonate from the urea hydrolysis then combines with $H^+$ to form bicarbonate ($HCO_3^-$) and carbonic acid ($H_2CO_3$). Carbonic acid is an unstable organic acid; most of it quickly breaks down into water and carbon dioxide molecules ($CO_2$). The HZO (containing acetate as a counter ion) removes $HCO_3^-$, $P^-$, and other anions (e.g., $F^-$ in water), and releases acetate. The activated carbon absorbs organic metabolites such as creatine, uric acid, and nitrogenous metabolic waste of the patient as well as chlorine and chloramines from the water. The $CO_2$ gas bubbles are vented from the cartridge.

The safety and efficacy record of the REDY system has been well established. Nevertheless, the REDY cartridge can produce a variation of dialysate composition and pH during the treatment with the production of bicarbonate and carbonic acid, and the continuous release of $Na^+$ by the cartridge.

Current zirconium phosphate (ZrP) based dialysis applications, such as the REDY cartridges, contain a large amount of lattice $H^+$ ions even when it is titrated to a pH range of 5.75-6.45. During sorbent dialysis, these lattice $H^+$ ions of ZrP will react with the $NaHCO_3$ in dialysate causing initial decomposition of bicarbonate to $CO_2$ gas and adsorption of $Na^+$. After depletion of $H^+$ ions and loading up of $Na^+$ in ZrP, progressively, the $NH_4$ adsorption mechanism will then switch to ion-exchange with adsorbed $Na^+$ in ZrP. This will cause increasing release of $Na^+$, accompanied by a rise of $HCO_3^-$-level, and formation of $CO_3^{2-}$ from urea hydrolysis. Consequently, the use of ZrP alone for sorbent dialysis can cause a variation in $Na^+$, $HCO_3^-$, and pH in regenerated dialysate during treatment.

The $Na^+$ and bicarbonate level in the dialysate can also vary depending on the blood urea nitrogen (BUN) level of the patient. Thus, the REDY dialysis therapy has to provide several dialysate prescriptions to balance the pH and the $Na^+$ level in the patient for the correction of hyper and hyponatremia. Also a conductivity alarm system is generally present to keep the $Na^+$ level in the dialysate below a safe limit.

A need exists for ion-exchange materials for sorbent dialysis systems that can maintain steady and predictable dialysate compositions. Sorbent cartridges containing such materials could regenerate spent dialysate to normal and balanced $Na^+$, $HCO_3^-$ and pH levels, and without formation of $CO_2$ gas bubbles. A need also exists for ion-exchange materials and sorbent dialysis systems that can remove toxic metal and non-metal ions from tap water in preparation of purified dialysate for dialysis.

SUMMARY OF THE PRESENT INVENTION

A feature of the present invention is to provide a sorbent cartridge that avoids one or more of the above mentioned disadvantages.

Another feature of the present invention is to provide a sorbent cartridge that can regenerate spent dialysate and restore the levels of $Na^+$ and $HCO_3^-$ to levels found in fresh dialysate.

Another feature of the present invention is to provide an improved ion-exchange material that releases a controlled amount of $Na^+$ ions.

A further feature of the present invention is to provide a method of regenerating spent dialysate without release of $Na^+$ ions to the dialysate.

An additional feature of the present invention is to provide a dialysis system that maintains a uniform level of $Na^+$ in the dialysate.

Additional advantages of the present invention will be set forth in part in the description that follows, and in part will be apparent from the description, or may be learned by practice of the present invention. The goals and advantages of the present invention will be realized and attained by means of the elements particularly pointed out in the appended claims.

To achieve the above noted goals and in accordance with the purposes of the present invention, as embodied and broadly described herein, the present invention provides a sorbent cartridge comprising a combination of acid zirconium phosphate (AZP) and alkaline hydrous zirconium oxide (NaHZO) in the sorbent cartridge. The combination of AZP and NaHZO can be present as a homogeneous mixture wherein the AZP and the NaHZO are uniformly distributed as a layer in the sorbent cartridge. The combination of AZP and NaHZO can provide functional properties to the sorbent cartridge that may not be present in sorbent cartridges comprising separate layers of ZrP and HZO.

The present invention also provides a sorbent cartridge comprising a combination of AZP and NaHZO in the cartridge, wherein the ratio of AZP to NaHZO can be varied, for example, to control the pH of regenerated dialysate, and/or to obtain the desired amount of sodium binding.

The present invention further provides a sorbent cartridge that can be used in an apparatus and/or system for conducting dialysis, for example, hemodialysis and/or peritoneal dialysis.

The present invention further provides a sorbent cartridge comprising a combination of AZP and NaHZO, and optionally further comprising ZrP. The ZrP can be titrated to a selected pH to control the functional characteristics of the sorbent cartridge, for example, the desired amount of sodium binding.

The present invention also provides a sorbent cartridge that is configured to restore the balance of $Na^+$ and $HCO_3^-$ in spent dialysate to levels found in fresh dialysate.

The present invention further provides a method to regenerate or purify spent dialysate without releasing $Na^+$, and/or generating $CO_2$ gas bubbles, in the dialysate.

The present invention also provides a method of preparing purified dialysate for dialysis.

The present invention further provides a dialysis system that can regenerate spent dialysate while maintaining a uniform level of $Na^+$ in the dialysate.

It is to be understood that both the foregoing general description and the following detailed description are exemplary only and are not restrictive of the present invention, as claimed.

BRIEF DESCRIPTION OF THE DRAWINGS

FIG. 1A is a schematic diagram of sorbent cartridges according to various embodiments.

FIG. 1B is a schematic diagram of sorbent cartridges according to various embodiments.

FIG. 2 is a schematic diagram of a sorbent cartridge according to various embodiments.

DETAILED DESCRIPTION OF THE INVENTION

Figure 3:
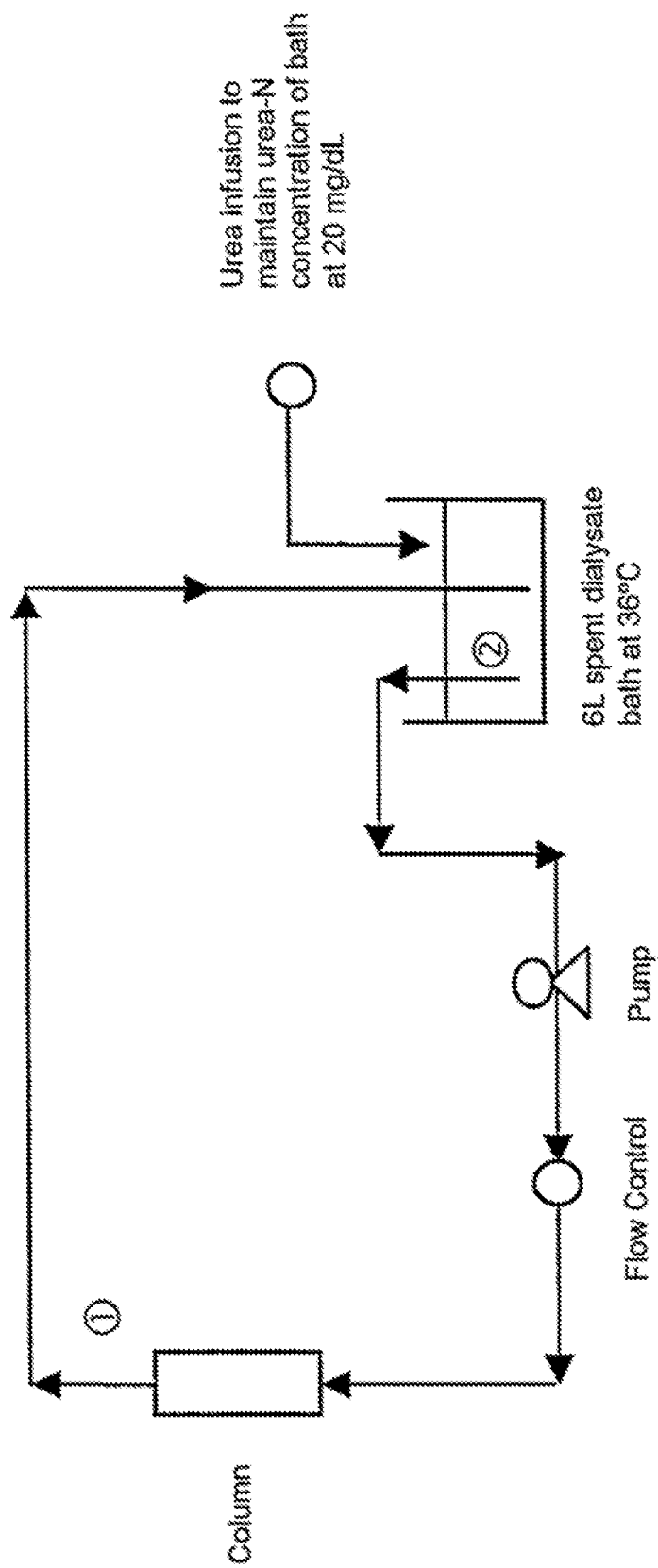
FIG. 3 is a schematic diagram of a dialysis recirculation system.

The present invention relates to materials useful for the removal of waste products and excess fluid that accumulates in dialysate fluids. These materials can be present in a container (e.g., a sorbent cartridge) capable of holding the materials useful for the removal process. The materials described in detail below, or the arrangement of materials, can be used in a dialysis system or other similar type of system that is useful for the removal of waste products and/or excess fluid that accumulates in dialysate fluids, for instance, as a result of conducting hemodialysis or peritoneal dialysis. As described in more detail below, the present invention is useful in purifying or regenerating dialysate used in hemodialysis and in peritoneal dialysis. Conventional dialysis solutions for peritoneal dialysis or hemodialysis can be used and regenerated by the present invention and are known to those skilled in the art.

The present invention, in part, relates to a sorbent cartridge comprising a combination of acid zirconium phosphate (AZP) and alkaline hydrous zirconium oxide (NaHZO) in the sorbent cartridge. For purposes of the present invention, acid zirconium phosphate, or AZP, means the $H^+$ form of zirconium phosphate. AZP can have the following chemical and physical properties:

Composition: $(H^+)_x(ZrO_2)(OH^-)_y(PO_4)_{1.8-2.0} \cdot nH_2O$
Ion-exchange formula: $[ZrO_2(OH)_y(PO_4)_2]^{2-} \cdot H^+_x$
Structural formula:

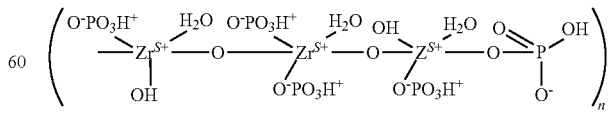

wherein x for $H^+$ is 1.5 to 2.0, y for $OH^-$ is 0.5 to 0, and n for $H_2O$ and for the structural formula is 1 to 4. x, y, and n can be any decimal in these ranges and can optionally be above or below these ranges. The AZP can have a hydrogen ion content of, for example, from about 2-10 mEq $H^+$/g AZP, from about 4-8 mEq $H^+$/g AZP, or from about 5-7 mEq $H^+$/g AZP. The AZP can have a pH in water (1 g/100 ml) of, for example, about 0.5-5, or about 1-3, and a pH in brine (1 g/100 ml) of, for example, about 0-5, or about 0.5-1.5.

For purposes of the present invention, alkaline hydrous zirconium oxide, or NaHZO, means the alkaline form of hydrous zirconium oxide ($ZrO(OH)_2$), in which the zirconium oxide is hydroxylated. NaHZO can have the following chemical and physical properties:

Composition: $Na^+_x ZrO_2(OH^-)_y \cdot nH_2O$
Ion-exchange formula: $ZrO_2 \cdot OH^-$
Structural formula:

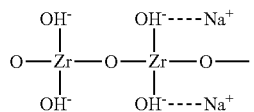

wherein x for $Na^+$ is 1, y for $OH^-$ is 2 to 4 and n for $H_2O$ is 4 to 6, and x, y, and n can be any decimal in these ranges and can optionally be above or below these ranges. The NaHZO can have a $Na^+$ content $Na:ZrO_2$ (molar ratio) in a range of, for example, from about 0.5:1.5, about 1:1, or about 1.5:0.5, and/or have a hydroxyl ion content in a range of, for example, about 3-12 mEq $OH^-$/10 g NaHZO, about 5-10 mEq $OH^-$/10 g NaHZO, or about 6-9 mEq $OH^-$/10 g NaHZO. The NaHZO can have a pH in water (1 g/100 ml) of, for example, about 7-14, about 9-12, or about 10-11.

The present invention, in part, is based on the following mechanisms: (1) conversion of carbonic acid and $CO_2$ gas back to $HCO_3^-$ by the alkaline NaHZO after $NaHCO_3$ is decomposed by AZP, and/or (2) switch of the ion-exchange mechanism from adsorbed $Na^+$ of ZrP to lattice $H^+$ ions of AZP so that there is no release of $Na^+$. For example:

AZP:

NaHZO:

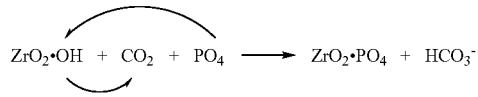

It was determined that the cationic ion-exchange properties of the $H^+$ form of ZrP (i.e. AZP) when acting alone, for example, in a separate layer in a sorbent cartridge, does not readily release $H^+$ in exchange for $NH_4^+$, $Ca^{2+}$, $K^+$, $Mg^{2+}$, $Na^+$, and other cations that may be present in spent dialysate. It was further determined that when in the presence of base, for example $OH^-$, $HCO_3^-$, or $CO_3^{2-}$, the base can serve to extract the $H^+$ ions out from AZP which are then replaced by the cation adsorbed. Accordingly, when blended with NaHZO, for example, as a homogeneous mixture, the ion-exchange properties of AZP can be affected. The ability of AZP, for example, to release $H^+$ in exchange for other cations increases. A combination of AZP and NaHZO can efficiently absorb cations from spent dialysate. Without wishing to be bound to any theory, one possible reason may be that the $OH^-$ groups present in NaHZO, and their interaction with $H^+$ in AZP, may be responsible for the altered ion-exchange properties.

The anionic ion-exchange properties of NaHZO, having adsorption capacities for $PO_4^{2-}$, $F^-$, $SO_4^{2-}$ and other anions, can be altered when acted upon by an acidic pH, for example, a pH less than 7. In the presence of acid, the NaHZO can be alkaline in water, releasing $OH^-$ ions in exchange for adsorption of other anions. The release of $OH^-$ ions can remove acid entities from water ($CO_2$ gas or $H^+$ ions) and keep the pH in the neutral range (e.g., pH of 7 to 7.4).

The combination of AZP and NaHZO can also precisely control $HCO_3^-$ by controlling the pH in regenerated dialysate in the range of, for example, pH 3-4, and removing most (e.g., to a negligible amount) or all of the carbonic acid and $CO_2$. As a result, a desired amount of $HCO_3^-$ can then be proportioned back in to the dialysate, for example, at about 35 mEq/L. The $Na^+$ level can also be maintained constant in the dialysate due to the switch to the $H^+$ ion-exchange mechanism of AZP.

The present invention relates, in part, to a combination of AZP and NaHZO in a sorbent cartridge. The AZP/NaHZO combination can prevent variation of $Na^+$, $HCO_3^-$ and pH in regenerated dialysate during dialysis treatment. The alkaline NaHZO can convert carbonic acid and $CO_2$ back to $NaHCO_3$ so that bicarbonate level and pH are unchanged. The ion-exchange of $NH_4^+$, and electrolyte cations $K^+$, $Ca^{2+}$, and $Mg^{2+}$, can switch from $Na^+$ to AZP lattice $H^+$ ions throughout the dialysis treatment. Thus, AZP can control $Na^+$ variation in dialysate by binding and removing $Na^+$ ions from dialysate, and by not releasing $Na^+$ to the dialysate.

The present invention also relates, in part, to combinations of AZP and NaHZO wherein the ratio of AZP to NaHZO can be varied. By lowering the proportion of NaHZO, the combination of AZP and NaHZO can control the pH of regenerated dialysate, for example, in the pH range of about 3-4. In this pH range, the bicarbonate in regenerated dialysate can be completely converted to carbonic acid and $CO_2$ gas. Subsequently, precise bicarbonate control can be accomplished by proportioning in $NaHCO_3$, for example, at a level of about 35 mEq/L, and thus restoring the pH back to a desired level, for example, physiological level, or a pH of about 7-7.4.

The combination of AZP and NaHZO can be present together in the cartridge as at least one layer. The sorbent cartridge can comprise at least two layers and the cartridge can comprise at least one other layer of sorbent material. The combination of AZP and NaHZO can be present in the sorbent cartridge as AZP particles and NaHZO particles having an average size, for example, of from about 25 microns to about 60 microns. The combination of AZP and NaHZO can be present as a homogeneous mixture, wherein the AZP and the NaHZO are uniformly distributed or mixed amongst each other, for instance, as one or more layers, in the sorbent cartridge.

A sorbent cartridge comprising a combination of AZP and NaHZO in the sorbent cartridge can regenerate spent dialysate preferably without releasing $Na^+$ ions. The combination of AZP and NaHZO can also serve as a uremic toxin adsorbent to remove urea ($NH_4^+$ after urea hydrolysis by urease) and phosphate from spent dialysate.

The AZP can be prepared by a reaction between aqueous solutions of a zirconium salt and phosphoric acid. The reaction forms a gelatinous precipitate that is filtered and washed until excessive phosphoric acid is removed, and then dried in an oven, such as to a moisture level of from about 12 to 18 weight percent Loss on Drying (LOD). Other LODs are possible. The final product after drying can be a fine powder or granules, such as with an irregular form. The AZP can comprise, for example, particles having an average particle size of about 5-100 microns, about 10-80 microns, about 25-60 microns, or about 25-45 microns. The average grain size is not limited to these ranges and can be sizes above or below these ranges.

The AZP can be prepared, for example, by following the methods disclosed in U.S. Pat. No. 6,818,196, which is incorporated in its entirety by reference herein. Briefly, AZP can be prepared by heating zirconium oxychloride (ZOC) with soda ash to form sodium zirconium carbonate, and treating the sodium zirconium carbonate with caustic soda to form alkaline hydrous zirconium oxide. An aqueous slurry of the alkaline hydrous zirconium oxide can then be heated while adding phosphoric acid and an acid zirconium phosphate recovered. An aqueous slurry of the AZP can also be titrated with a basic agent, such as caustic soda, until a desired pH is reached, for example, a pH of from about 5 to about 7.

Alternatively, the AZP can be prepared by heating an aqueous mixture of basic zirconium sulfate (BZS) and phosphoric acid at a sufficient temperature (e.g., 180° F.-190° F.) and for a sufficient time (e.g., 1-2 hr) to form acid zirconium phosphate precipitate. Then the solution can be cooled and the acid zirconium phosphate can be filtered and washed to reduce unreacted leachable phosphate levels. The AZP particles can be further dried, for example, at about 120° F.-170° F. The AZP particles can have a BET surface area of less than 2 m$^2$/g. By way of example, the AZP can be prepared as described in Example 1.

The AZP can be prepared, for example, by following the methods disclosed in U.S. Patent Application Publication 2006/0140840, which is incorporated in its entirety by reference herein in combination with the teachings provided herein. Briefly, AZP can be prepared by preparing a solution of zirconium oxychloride (ZOC) and an organic chemical additive in water, and then titrating with concentrated hydrochloric acid (HCl) to fully dissolve the precipitate. This ZOC solution is then added to a solution of phosphoric acid to produce a slurry of AZP precipitate. The precipitate is then filtered and washed. The AZP particles can have a BET surface area greater than 10 m$^2$/g. By way of example, AZP can be prepared as described in Example 2.

Alkaline hydrous zirconium oxide can be prepared by the reaction of a zirconium salt, for example, BZS, or its solution in water with an alkali metal (or alkali metal compound) at ambient temperature, to form a NaHZO precipitate. The NaHZO particles can be filtered and washed until the anions of the zirconium salt are completely removed, and then preferably air dried, or dried in an oven at mild temperature (e.g., 60° F. to less than 90° F.) to a moisture level, for instance, of from about 25-30 weight percent LOD or lower, to form a free-flowing powder. Other LODs can be achieved, although higher temperature (e.g. 90° F.-120° F.) and/or long drying time (e.g. 24-48 hrs) to achieve a lower moisture level (i.e., <20 weight percent LOD) can convert the zirconium-hydroxide bond to a zirconium-oxide bond and reduce the adsorption capacity as well as alkalinity of the anion-exchange material. The drying temperatures refer to the nominal temperature in the oven or dryer. The NaHZO can comprise particles having an average grain size of about 10-100 microns, about 20-80 microns, about 25-60 microns, or about 25-40 microns. The average grain size is not limited to these ranges and can be sizes above or below these ranges. The NaHZO can have a BET surface area of less than 2 m$^2$/g (e.g., 0.1 to 1.9 m$^2$/g, 0.5 to 1.5 m$^2$/g, 0.8 to 1.2 m$^2$/g). By way of example, the NaHZO can be prepared as described in Example 3.

The NaHZO can be prepared, for example, by following the methods disclosed in U.S. Patent Application Publication 2006/0140840, which is incorporated in its entirety by reference herein, in combination with the teachings provided herein. Briefly, this method of preparing NaHZO involves adding an aqueous solution of ZOC, titrated with concentrated HCl, to an aqueous solution of caustic soda. The HCl addition can prevent excessive gelation during the precipitation process as well as to promote particle growth. The NaHZO particles can have a BET surface area of greater than 10 m$^2$/g. By way of example, the NaHZO can be prepared as described in Example 4.

The AZP and NaHZO of the present invention can be present as a layer (or layers) in sorbent cartridges such as those described in U.S. Pat. No. 7,033,498 B2, and U.S. Pat. No. 6,878,283 B2, in Sorb Technology's REDY cartridge, and in Renal Solution's Allient cartridge (e.g., see "Sorbent Dialysis Primer," COBE Renal Care, Inc. Sep. 4, 1993 edition), all incorporated in their entirety by reference herein. For example, various filter media sections within a tubular housing or cartridge can be used with the AZP and NaHZO of the present invention. The housing or cartridge can include a sorbent material like a granular activated carbon section, an immobilized enzyme section, a powdered alumina ($Al_2O_3$) section, and/or a zirconium phosphate (ZrP) section, or any combinations thereof. The ZrP can be prepared, for example, as described in U.S. Published Patent Application No. 2006/0140840, incorporated in its entirety by reference herein. The amounts for each component can be as stated in the above patents and exemplary amounts are provided in the figures. Depending on the application, the AZP/NaHZO layer can be used in an amount, for example, of from about 200-1700 g per dialysis cartridge, such as from about 500-600 g per cartridge used in hemodialysis, or from about 200-1200 g per cartridge used in peritoneal dialysis.

The AZP and NaHZO can be present in any desired weight ratio. The weight ratio of NaHZO:AZP can range, for example, from about 0.1:0.9 to about 0.9:0.1, from about 0.2:0.8 to about 0.8:0.2, from about 0.22:0.78 to about 0.33:0.67, from about 0.5:0.5 to about 0.6:0.4, or about 0.4:0.6. The various weight ratios of AZP and NaHZO can provide a mixture having any desired pH. A mixture of AZP and NaHZO can have a pH, for example, from about 3 to about 9, from about 3 to about 7, from about 3.5 to about 4, from about 4 to about 5.5, or from about 5.5 to about 6.

The sorbent cartridge can further comprise ZrP. The ZrP can be present as a separate layer(s) in the sorbent cartridge. The ZrP can be titrated to have any desired pH, for example, a pH from about 3 to about 9, from about 3 to about 7, from about 3.5 to about 4, from about 4 to about 5.5, or from about 5.5 to about 6. Sorbent cartridges comprising a combination of AZP and NaHZO in various amounts and ratios, and in various pH levels, and/or providing ZrP in a variety of pH levels, can provide desired effects on the performance of dialysate regeneration, as further detailed below.

The sorbent cartridge can further comprise activated carbon, enzyme, alumina, or combinations thereof. The activated carbon, enzyme, and/or alumina can each be present as separate layers in the sorbent cartridge. The enzyme can be, for example, urease, and the enzyme can be immobilized.

The sorbent cartridge can be a cartridge that contains one or more layers or zones of the AZP particles and NaHZO particles, wherein the sorbent cartridge has a plurality of filter media sections (or layers) including an arrangement, starting from a first end (inlet) and ending at a second end (outlet), an activated carbon section, an immobilized enzyme section, a powdered alumina section, and an AZP/NaHZO section (for example, as a composite). The arrangement can optionally further include a ZrP section located before and/or after the AZP/NaHZO section, and/or can optionally include a sodium zirconium carbonate layer before and/or after the AZP/NaHZO section.

The composition of the present invention can be used in any application in sorbent cartridges as a layer with one or more layers described for instance in U.S. Published Patent Application No. 2002-0112609 and U.S. Pat. No. 6,878,283 B2, and in Sorb's REDY cartridge (e.g., see "Sorbent Dialysis Primer," COBE Renal Care, Inc. Sep. 4, 1993 edition, and "Rx Guide to Custom Dialysis," COBE Renal Care, Inc. Revision E, September, 1993), all incorporated in their entirety by reference herein. For example purposes only, various filter media sections within a tubular housing or cartridge can be used with the composition of the present invention. The composition of the present invention can be used in combination with or in place of any zirconium phosphate layer. The composition of the present invention can be used as a layer in the sorbent cartridge described in U.S. Pat. Nos. 6,627,164; 6,878,283; 7,033,498; or published Application No. 2006/0140840, incorporated by reference herein.

For dialysis, a filter medium adapted to remove chlorine from tap water is preferred unless purified water is used as a base for the dialysate. The filter medium can be activated carbon. Activated carbon can also be used as a filter medium to bind heavy metals, oxidants, and chloramines. An immobilized enzyme such as urease can be used in a filter medium to convert urea to ammonium carbonate by enzymatic conversion. Urease can be immobilized by adsorption, covalent bonding, intermolecular cross-linking, entrapment within cross-linked polymers, microencapsulation, and containment within a semipermeable membrane device. Alumina ($Al_2O_3$), activated carbon, anion-exchange resins, and diatomaceous earth can be used as adsorbents. The use of activated carbon to remove chlorine, if used, can precede the immobilized enzyme medium because chlorine can deactivate the enzyme. Cation exchange materials can be used to bind ammonium, calcium, magnesium, potassium, and other cations as well as toxic trace metals in tap water. Such cation exchange materials can include AZP and ZrP. Anion exchange materials can bind phosphate, fluoride, and other heavy metals. Such anion exchange materials can include NaHZO.

Sorbent cartridges for regenerative dialysis can be configured as shown, for example, in FIG. 1A and in FIG. 1B. In FIG. 1A, a sorbent cartridge (Model I) can comprise a carbon layer, an immobilized urease layer, and an AZP and NaHZO combination (NaHZO/AZP layer) in the sorbent cartridge. In the top example of FIG. 1A, the AZP and NaHZO can be present in the sorbent cartridge in an amount and proportion such that the weight ratio of NaHZO:AZP is in a range of from about 0.5:0.5 to about 0.6:0.4. In such a configuration, the amount and ratio of AZP and NaHZO can be adjusted to obtain a uniform concentration of $Na^+$, $HCO_3^-$, and a pH of about 5.5-6.0. In the bottom example of FIG. 1A, the AZP and NaHZO can be present in the sorbent cartridge in an amount and proportion such that the weight ratio of NaHZO:AZP is in a range of from about 0.22:0.78 to about 0.33:0.67. In such a configuration, the amount and proportion of AZP and NaHZO can be adjusted to obtain a uniform concentration of $Na^+$, a pH of 3-4, and complete removal of $HCO_3^-$.

As shown by the examples in FIG. 1B, a sorbent cartridge (Model II) can comprise a carbon layer, an immobilized urease layer, an AZP and NaHZO combination layer, and a ZrP layer in the sorbent cartridge. The ZrP layer can be titrated to a desired pH. The amount and proportion of AZP and NaHZO, and the amount and pH of titrated ZrP, can be adjusted to obtain a uniform concentration of $Na^+$ and $HCO_3^-$, and a desired uniform pH level. In the top example of FIG. 1B, the AZP and NaHZO can be present in the sorbent cartridge in an amount and proportion such that the weight ratio of NaHZO:AZP is in a range of from about 0.5:0.5 to about 0.6:0.4, and the ZrP can be titrated in a range of from about pH 5.5-6.0. In the bottom example of FIG. 1B, the AZP and NaHZO can be present in the sorbent cartridge in an amount and proportion such that the weight ratio of NaHZO:AZP is about 0.4:0.6, and the ZrP can be titrated in a range of from about pH 3.5-4.0. In such a configuration, a uniform concentration of $Na^+$, a pH of 3.5-4, and complete removal of $HCO_3^-$, can be obtained.

A sorbent cartridge comprising a combination of AZP and NaHZO in the sorbent cartridge can be capable of restoring the balance of $Na^+$ and $HCO_3^-$ in spent dialysate to the levels found in fresh dialysate. The sorbent cartridge can comprise a composite of AZP and NaHZO as detailed above. A sorbent cartridge comprising an AZP/NaHZO composite can effectively remove $NH_4^+$ and other cations from spent dialysate without releasing $Na^+$ ions, and without producing $CO_2$ gas bubbles.

A sorbent cartridge comprising a combination of AZP and NaHZO as detailed above can be utilized to regenerate or purify spent dialysate. A method to regenerate or purify spent dialysate can comprise passing the spent dialysate through a sorbent cartridge comprising a combination of AZP and NaHZO, as detailed above. In some methods, the sorbent cartridge can further comprise ZrP.

In some methods, the spent dialysate can be regenerated to essentially restore the original balance of $Na^+$ and $HCO_3^-$ contents found in fresh dialysate. The spent dialysate can be regenerated to comprise a $Na^+$ content of, for example, from about 90 mEq/L to about 180 mEq/L, from about 100 mEq/L to about 160 mEq/L, or from about 110 mEq/L to about 150 mEq/L. The spent dialysate can be regenerated to comprise a $HCO_3^-$ content of, for example, from about 20 mEq/L to about 40 mEq/L, from about 22 mEq/L to about 38 mEq/L, or from about 25 mEq/L to about 35 mEq/L. In some methods, the spent dialysate can be regenerated to essentially restore the original pH of fresh dialysate. The dialysate can be regenerated to a pH, for example, of from about 6.5 to about 8, or from about 6.8 to about 7.4. The dialysate can be regenerated or purified without release of $Na^+$ to the dialysate.

The dialysate can be regenerated with little or no generation of $CO_2$ gas bubbles. Spent dialysate can be passed through a sorbent cartridge comprising a combination of AZP and NaHZO as detailed above. The $NaHCO_3$ present in the spent dialysate can be decomposed by the AZP to form carbonic acid and $CO_2$. Then, at acidic pH, (e.g. pH <6.5) the carbonic acid and the $CO_2$ can be converted by the NaHZO to form $NaHCO_3$.

A sorbent cartridge comprising a combination of AZP and NaHZO as detailed above can be utilized to prepare purified dialysate for dialysis. The dialysate can comprise tap water. The sorbent cartridge can act as a dialysate purification system. Dialysate levels of bacteria and endotoxin can be maintained, for example, at <1 CFU/ml bacteria and <0.3 EU/ml endotoxin.

An apparatus for conducting dialysis can comprise a sorbent cartridge comprising a combination of AZP and NaHZO as detailed above, and a dialyzer in fluid communication with the sorbent cartridge, wherein spent dialysate passes from the dialyzer to and through the sorbent cartridge. The spent dialysate can be spent hemodialysate, spent peritoneal dialysate, or combinations thereof. The dialyzer can be in fluid communication with the blood of a patient.

A dialysis system can comprise a sorbent cartridge comprising a combination of AZP and NaHZO as detailed above, and a source of spent dialysate, wherein the source of the spent dialysate is in fluid communication with the sorbent cartridge and the spent dialysate passes to and through the sorbent cartridge. The spent dialysate can pass through the sorbent cartridge at a rate of from about 10 ml/min to about 1000 ml/min, from about 100 ml/min to about 550 ml/min, or from about 150 ml/min to about 400 ml/min. The dialysis system can regenerate the spent dialysate, and can regenerate the spent dialysate to a pH level approximately equal to that of fresh dialysate. The system can also regenerate the spent dialysate without the formation of $CO_2$ gas bubbles. The system can furthermore maintain a uniform level of $Na^+$ while the spent dialysate is being regenerated.

The following examples are given to illustrate the nature of the invention. It should be understood, however, that the present invention is not limited to the specific conditions or details set forth in these examples.

EXAMPLES

Example 1

One (1) kg of BZS was added to deionized water in a reactor to form a slurry with moderate agitation speed. Then, about 770 ml Technical Grade phosphoric acid (76%) diluted with equal volume of water was pumped into the slurry. With slow agitation, the slurry was heated at moderate or maximum rate to 180-185° F., and then heated to maintain that temperature for one hour after the temperature was reached. The slurry was then cooled to room temperature. The product was filtered and washed in a Buchnell funnel with deionized water. The filter cake was then dried in a tray dryer at 180° F. until the moisture level was 12-18 weight percent LOD. The particle size was in a range of from 25-60 microns.

Example 2

Solution A was prepared as follows: 20 g ZOC crystals was dissolved in 15 ml deionized water and 15 ml isopropanol was added to the solution. Then, with agitation by magnetic stirrer or plastic impeller, about 100 drops of concentrated HCl was added to the solution with continued agitation until all precipitate was redissolved to form a clear solution.

Solution B was prepared as follows: 30 g Technical Grade phosphoric acid (76%) was diluted in 60 ml water in a 500 ml beaker. With a magnetic stirrer, the diluted acid was heated to a boiling temperature.

Reaction process steps:
Step 1: Solution A was pumped into Solution B at boiling temperature at about 10 ml/min flow rate, with moderate agitation speed using magnetic stirrer or plastic impeller.
Step 2: After addition was complete to produce a slurry of precipitate, the slurry was heated for one hour to evaporate off the alcohol completely and improve crystal structure of the AZP precipitate.
Step 3: After heating for one hour, the slurry was allowed to cool. The precipitate was then filtered and washed with deionized water to remove excessive unreacted phosphoric acid.
Step 4: The washed product was dried in an oven at 180° F. until the moisture level was 5-20 weight percent LOD to form a free-flowing powder. The particle size was in a range of from 25-45 microns.

Example 3

500 g BZS was added to 430 ml deionized water in a 1-liter beaker to form a slurry with mild agitation. Then 40 ml 50% NaOH was added to the slurry to elevate the pH to about 6.5. The material was filtered and washed 3 times with 500 ml deionized water in a Buchnell funnel. With mild agitation, the filter cake was transferred to an alkali solution with higher alkaline strength made up by mixing 140 ml 50% NaOH with 125 ml deionized water. The pH of the slurry was checked and an additional amount of NaOH was added if necessary to obtain pH above 12.5. The slurry was then agitated for 30 minutes. The product was filtered in a Buchnell funnel fitted with glass fiber filter then washed with deionized water until the leachable sulfate could not be detected in the filtrate by applying the $BaCl_2$ reagent test. The filter cake was transferred to a tray dryer at approximately 110° F. and the material dried to a moisture level of about 25 to 30 weight percent LOD to form a free-flowing powder. The particle size was in a range of from 25 to 60 microns.

Example 4

Solution A was prepared as follows: 20 g ZOC crystals was dissolved in 50 ml deionized water at room temperature. Approximately 100 drops of concentrated HCl was added to the solution with mild agitation using a magnetic stir bar.

Solution B was prepared as follows: 100 ml Technical Grade caustic soda (50% NaOH) was diluted with 300 ml deionized water in a 500 ml beaker at room temperature to obtain approximately a 12.5% NaOH solution (about 3N).

Reaction process steps:
Step 1: Solution A was pumped into Solution B at room temperature at the flow rate of about 10 ml/min with vigorous agitation speed using a magnetic stirrer or plastic impeller. The pH was monitored during the precipitation process to ensure the pH was still above 12.0 at the end.
Step 2: After addition was complete to produce a slurry of precipitate, the vigorous agitation was continued for 30 minutes to allow the particles to become hardened.
Step 3: The filter cake was transferred to a tray dryer at about 110° F. and the material dried to the moisture level of approximately 25 to 35 weight percent LOD to form a free-flowing powder. The particle size was in a range of about 25-40 microns.

Example 5

Cartridge effluent with $Na^+$, $HCO_3^-$, and pH restored to normal range.

Step 1: A column was prepared with the configuration as shown in FIG. 2 (2-inch diameter polycarbonate column).
Step 2: A 6 L bath was prepared at approximately 36° C. to simulate spent dialysate (i.e., after passing through dialyzer) with a composition shown as follows:

| | |
|---|---|
| $Na^+$ | 135 mEq/L |
| $Mg^{2+}$ | 1 mEq/L |
| $Ca^{2+}$ | 3 mEq/L |
| $K^+$ | 2 mEq/L |
| $HCO_3^-$ | 30 mEq/L |
| pH | 7.0-7.4 |
| $Cl^-$ | 105 mEq/L |
| $PO_4$—P | 5 mg/dL |
| BUN | 20 mg/dL |
| Creatinine | 10 mg/dL |

Step 3: A recirculation system was set up as shown in FIG. 3

The spent dialysate was re-circulated through the column at a flow rate of about 80 ml/min. Urea was re-infused into the 6 L bath to maintain the urea-N concentration at about 20 mg/dL urea-N during the re-circulation. Ten ml samples of cartridge effluent were collected (at Location ① and 10 ml samples of the 6 L bath were collected (at Location ② according to the following schedule: Initial, 5 min, 10 min, 15 min, 30 min, 60 min, 120 min.

The time variation of dialysate composition in the cartridge effluent and the 6 L spent dialysate bath are shown in TABLE 1 and TABLE 2.

TABLE 1

Time variation of dialysate composition in cartridge effluent at Location ①

| Cartridge effluent at Location ① | pH | Na mEq/L | HCO$_3^-$ mEq/L | PO$_4$—P mg/dL | BUN mg/dL | NH$_4^+$—N mg/dL | Creatinine mg/dL | Ca$^{2+}$Mg$^{2+}$K$^+$ mEq/L |
|---|---|---|---|---|---|---|---|---|
| Initial | 7.12 | 129 | 31 | 0.13 | 0 | 0.03 | 0.2 | <0.2 |
| 5 min | 6.50 | 126 | 31 | 0.14 | 0 | 0.03 | 0.2 | <0.2 |
| 10 min | 6.20 | 130 | 29 | 0.20 | 0 | 0.03 | 0.2 | <0.2 |
| 15 min | 6.50 | 135 | 32 | 0.13 | 0 | 0.03 | 0.2 | <0.2 |
| 30 min | 6.56 | 136 | 30 | 0.20 | 0 | 0.03 | 0.2 | <0.2 |
| 60 min | 6.78 | 136 | 30 | 0.36 | 0 | 0.05 | 0.2 | <0.2 |
| 120 min | 7.46 | 141 | 36 | 0.10 | 0.2 | 2.22 | 0.2 | <0.2 |

TABLE 2

Time variation of dialysate composition in the 6 L spent dialysate bath at Location ②

| 6 L spent dialysate at Location ② | pH | Na mEq/L | HCO$_3^-$ mEq/L | PO$_4$—P mg/dL | BUN mg/dL (with re-infusion) | NH$_4^+$—N mg/dL | Creatinine mg/dL | Ca$^{2+}$ mEq/L | Mg$^{2+}$ mEq/L | K$^+$ mEq/L |
|---|---|---|---|---|---|---|---|---|---|---|
| Initial | 7.30 | 135 | 30 | 5 | 20 | — | 10 | 3 | 2 | 1 |
| 5 min | 7.29 | 129 | 32 | 0.30 | 19.4 | — | 2 | — | — | — |
| 10 min | 6.76 | 132 | 33 | 0.20 | 18.3 | — | 0.2 | — | — | — |
| 15 min | 6.61 | 133 | 30 | 0.15 | 16.5 | — | 0.2 | — | — | — |
| 30 min | 6.67 | 130 | 36 | 0.26 | 23.7 | — | 0.2 | — | — | — |
| 60 min | 6.72 | 130 | 34 | 0.13 | 26.8 | — | 0.2 | — | — | — |
| 120 min | 7.13 | 140 | 36 | 0.15 | 24.7 | — | 0.2 | — | — | — |

Example 6

The test in Example 5 was repeated by using 2 L spent dialysate bath instead. The time variation of the dialysate bath composition at Location ② is shown in TABLE 3.

TABLE 3

Time variation of dialysate composition in the 2 L spent dialysate bath at Location ②

| 2 L spent dialysate at Location ② | pH | Na mEq/L | HCO$_3^-$ mEq/L | PO$_4$—P mg/dL | BUN mg/dL (with re-infusion) | NH$_4^+$—N mg/dL | Creatinine mg/dL | Ca$^{2+}$ mEq/L | Mg$^{2+}$ mEq/L | K$^+$ mEq/L |
|---|---|---|---|---|---|---|---|---|---|---|
| Initial | 7.16 | 134 | 31 | 5 | 21 | — | 0.2 | 3 | 2 | 1 |
| 5 min | 7.23 | 129 | 33 | 0.23 | 17 | — | 0.2 | — | — | — |
| 10 min | 7.10 | 131 | 32 | 0.14 | 16 | — | 0.2 | — | — | — |
| 15 min | 6.71 | 129 | 28 | 0.11 | 18 | — | 0.2 | — | — | — |
| 30 min | 6.80 | 130 | 29 | 0.08 | 21 | — | 0.2 | — | — | — |
| 60 min | 6.68 | 131 | 27 | 0.07 | 22 | — | 0.2 | — | — | — |
| 120 min | 7.19 | 147 | 35 | 0.12 | 24 | — | 0.2 | — | — | — |

Example 7

The test in Example 5 was repeated by using 1 L spent dialysate bath instead. The time variation of the dialysate bath composition at Location ② is shown in TABLE 4.

TABLE 4

Time variation of dialysate composition in the 1 L spent dialysate bath at Location ②

| 1 L spent dialysate at Location ② | pH | Na mEq/L | HCO$_3^-$ mEq/L | PO$_4$—P mg/dL | BUN mg/dL (with re-infusion) | NH$_4^+$ mg/dL | Creatinine mg/dL | Ca$^{2+}$ mEq/L | Mg$^{2+}$ mEq/L | K$^+$ mEq/L |
|---|---|---|---|---|---|---|---|---|---|---|
| Initial | 7.02 | 133 | 31 | 5 | 18.7 | — | 0.2 | 3 | 2 | 1 |
| 5 min | 7.02 | 128 | 28 | 0.16 | 19.7 | — | 0.2 | — | — | — |

TABLE 4-continued

Time variation of dialysate composition in the 1 L spent dialysate bath at Location ②

| 1 L spent dialysate at Location ② | pH | Na mEq/L | $HCO_3^-$ mEq/L | $PO_4$—P mg/dL | BUN mg/dL (with re-infusion) | $NH_4^+$ mg/dL | Creatinine mg/dL | $Ca^{2+}$ mEq/L | $Mg^{2+}$ mEq/L | $K^+$ mEq/L |
|---|---|---|---|---|---|---|---|---|---|---|
| 10 min | 6.61 | 126 | 27 | 0.21 | 19.1 | — | 0.2 | — | — | — |
| 15 min | 6.80 | 125 | 24 | 0.08 | 23.7 | — | 0.2 | — | — | — |
| 30 min | 6.60 | 126 | 28 | 0.09 | 21.8 | — | 0.2 | — | — | — |
| 60 min | 6.60 | 128 | 29 | 0.10 | 25.4 | — | 0.2 | — | — | — |
| 120 min | 7.20 | 135 | 34 | 0.07 | 26.3 | — | 0.2 | — | — | — |

Example 8

Cartridge effluent with pH control at 2.4-3.0 by cartridge leading to complete $HCO_3^-$ removal by $CO_2$ degassing, followed by bicarbonate infusion to control $HCO_3^-$ level at 30-35 mEq/L.

Figure 4:
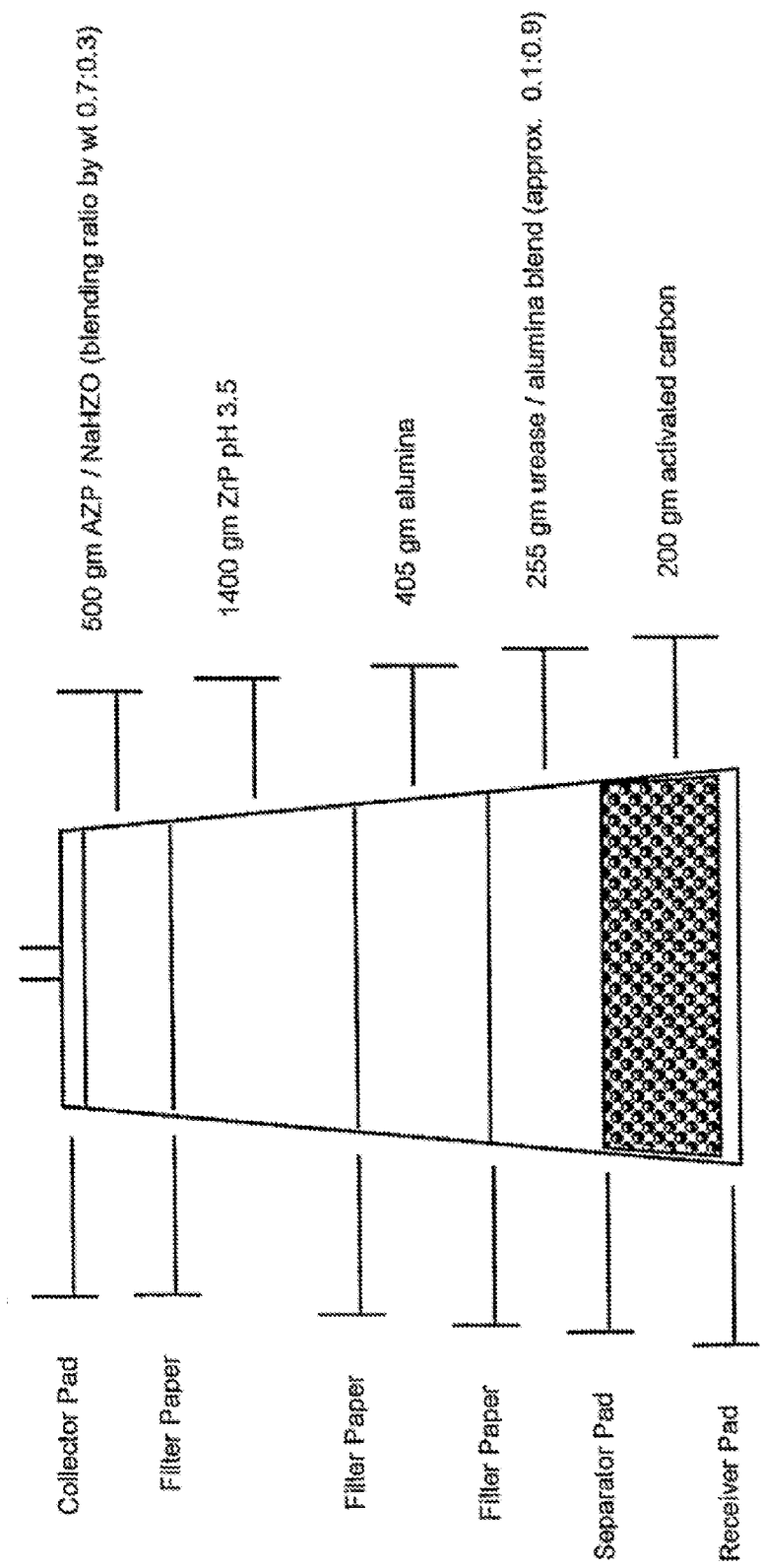
FIG. 4 is a schematic diagram of a sorbent cartridge according to various embodiments.

Step 1: A column was prepared with the configuration as shown in FIG. 4.

Step 2: A 144 L bath at approximately 36° C. was prepared to simulate spent dialysate for a 255 minute treatment time (i.e., after passing through dialyzer) with the composition shown below. This composition represented the actual fluid composition at the inlet of the cartridge throughout the actual treatment except for the varying BUN level during the treatment.

| | |
|---|---|
| $Na^+$ | 140 mEq/L |
| $HCO_3^-$ | 35 mEq/L |
| $Cl^-$ | 105 mEq/L |
| pH | 7.0-7.4 |
| $Mg^{2+}$ | 1 mEq/L |
| $Ca^{2+}$ | 3 mEq/L |
| $K^+$ | 2 mEq/L |
| $PO_4$—P | 2 mg/dL |

-continued

| | |
|---|---|
| BUN | 25 mg/dL |
| Creatinine | 20 mg/dL |

Figure 5:
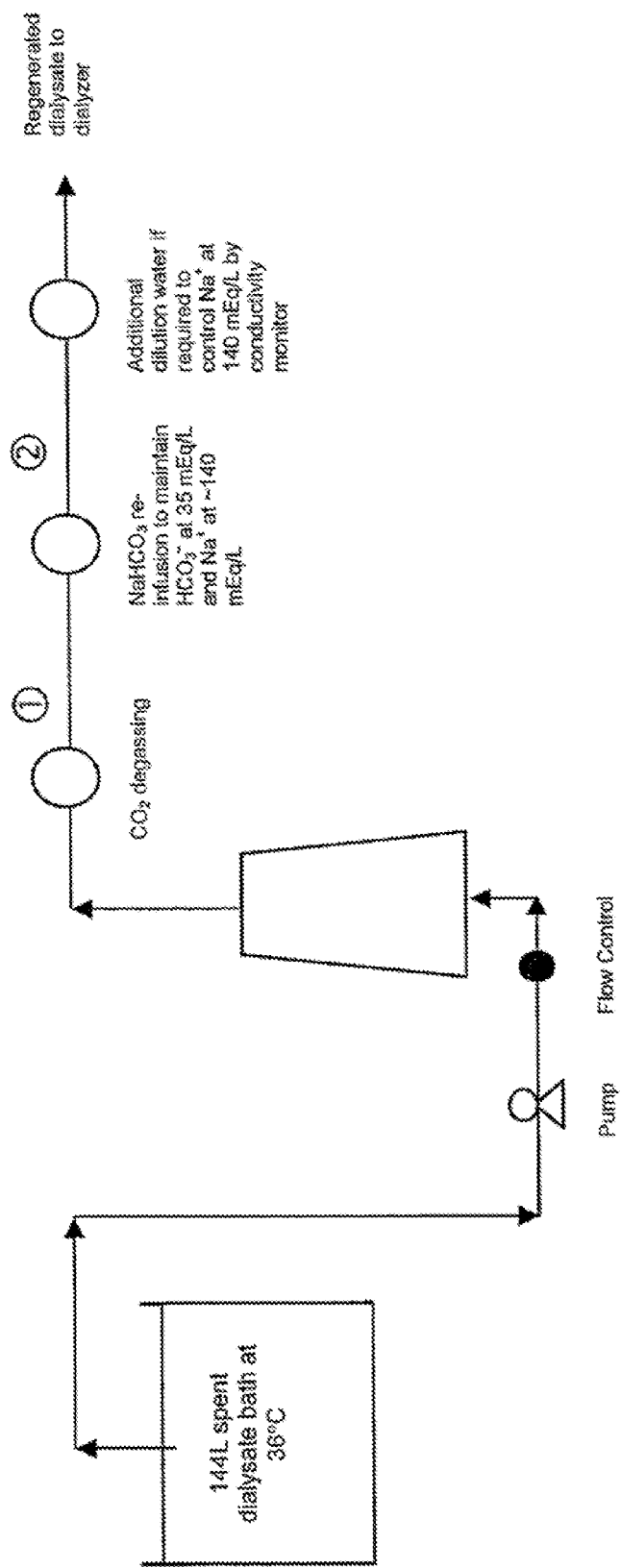
FIG. 5 is a schematic diagram of a single pass dialysis system.

Step 3: A single pass system was set up as shown in FIG. 5.

Step 4: The spent dialysate was pumped through the cartridge in the single pass mode at the flow rate of 550 ml/min. $NaHCO_3$ was re-infused to the bicarbonate-free dialysate after $CO_2$ degassing to restore and maintain bicarbonate level at 35 mEq/L. The $Na^+$ was also controlled at approximately 140 mEq/L by the additional $Na^+$ from $NaHCO_3$ (as well as increase the fluid volume from the infusate) before the regenerated dialysate was returned to the dialyser. Twenty (20) ml samples were collected from the bath, at Location ① before $NaHCO_3$ re-infusion, and at Location ② after $NaHCO_3$ re-infusion according to the following schedule: Location ① (before $NaHCO_3$ re-infusion)—initial, 10 min, 20 min, 30 min, 45 min, 60 min, 90 min, 120 min, 150 min, 180 min, 195 min, 210 min, 225 min, 240 min, 255 min; Location ② (after $NaHCO_3$ re-infusion)—30 min, 60 min, 120 min, 180 min.

The time variation of dialysate composition in the cartridge effluent before $NaHCO_3$ re-infusion at Location①, and after at Location②, are shown in TABLE 5 and TABLE 6.

TABLE 5

Dialysate composition data in the cartridge effluent after $CO_2$ degassing but before $NaHCO_3$ re-infusion at Location ①

| | Time (min) | | | | | | | |
|---|---|---|---|---|---|---|---|---|
| | 0 | 10 | 20 | 30 | 45 | 60 | 90 | 120 |
| $NH_4^+$ | 0 | 0 | 0 | 0 | 0 | 0 | 0 | 0 |
| pH | 6.03 | 2.40 | 2.40 | 2.41 | 2.37 | 2.44 | 2.58 | 2.58 |
| $Na^+$ (mEq/L) | 114 | 116 | 115 | 114 | 114 | 114 | 114 | 114 |
| $HCO_3^-$ (mEq/L) | 0 | 0 | 0 | 0 | 0 | 0 | 0 | 0 |
| $Cl^-$ (mEq/L) | 105 | 106 | 105 | 106 | 105 | 106 | 105 | 106 |
| $Ca^{2+}$ (mEq/L) | <0.2 | <0.2 | <0.2 | <0.2 | <0.2 | <0.2 | <0.2 | <0.2 |
| $K^+$ (mEq/L) | <0.2 | <0.2 | <0.2 | <0.2 | <0.2 | <0.2 | <0.2 | <0.2 |
| $Mg^{2+}$ (mEq/L) | <0.1 | <0.1 | <0.1 | <0.1 | <0.1 | <0.1 | <0.1 | <0.1 |
| BUN (mg/dL) | 0 | 0 | 0 | 0 | 0 | 0 | 0 | 0 |
| Creatinine (mg/dL) | <0.2 | <0.2 | <0.2 | <0.2 | <0.2 | <0.2 | <0.2 | <0.2 |
| $PO_4$-P (mg/dL) | 0.06 | 0.08 | 0.04 | 0.01 | 0.01 | 0.01 | 0.01 | 0.01 |

| | Time (min) | | | | | |
|---|---|---|---|---|---|---|
| | 150 | 180 | 195 | 210 | 225 | 240 | 255 |
| $NH_4^+$ | 0 | 0 | 0 | 0.1 | 0.1 | 0.1 | 0.3 |
| pH | 2.47 | 2.48 | 2.46 | 2.45 | 2.56 | 3.21 | 5.46 |

TABLE 5-continued

Dialysate composition data in the cartridge effluent after CO$_2$ degassing but before NaHCO$_3$ re-infusion at Location ①

| | | | | | | | |
|---|---|---|---|---|---|---|---|
| Na$^+$ (mEq/L) | 113 | 114 | 114 | 114 | 115 | 112 | 120 |
| HCO$_3^-$ (mEq/L) | 0 | 0 | 0 | 0 | 0 | 0 | 2.3 |
| Cl$^-$ (mEq/L) | 106 | 105 | 105 | 105 | 105 | 105 | 105 |
| Ca$^{2+}$ (mEq/L) | <0.2 | <0.2 | <0.2 | <0.2 | <0.2 | <0.2 | <0.2 |
| K$^+$ (mEq/L) | <0.2 | <0.2 | <0.2 | <0.2 | <0.2 | <0.2 | <0.2 |
| Mg$^{2+}$ (mEq/L) | <0.1 | <0.1 | <0.1 | <0.1 | <0.1 | <0.1 | <0.1 |
| BUN (mg/dL) | 0 | 0 | 0 | 0 | 0 | 0 | 0 |
| Creatinine (mg/dL) | <0.2 | <0.2 | <0.2 | <0.2 | <0.2 | <0.2 | <0.2 |
| PO$_4$–P (mg/dL) | 0.01 | 0.03 | 0.02 | 0.01 | 0.2 | 0.6 | 1.37 |

TABLE 6

Na$^+$ and HCO$_3^-$ levels in the cartridge effluent after NaHCO$_3$ re-infusion at Location ②

| | Time (min) | | | |
|---|---|---|---|---|
| | 30 | 60 | 120 | 180 |
| pH | 7.08 | 7.02 | 7.10 | 7.19 |
| Na$^+$ (mEq/L) (after dilution by re-infusion) | 142 | 142 | 142 | 142 |
| HCO$_3^-$ (mEq/L) | 33 | 33.5 | 34 | 34.5 |

TABLE 8

Na$^+$ and HCO$_3^-$ levels in the cartridge effluent after NaHCO$_3$ re-infusion at Location ②

| | Time (min) | | | |
|---|---|---|---|---|
| | 30 | 60 | 120 | 180 |
| pH | 7.01 | 7.04 | 7.15 | 7.20 |
| Na$^+$ (mEq/L) (after dilution by re-infusion) | 142 | 143 | 142 | 142 |
| HCO$_3^-$ (mEq/L) | 31 | 32 | 31 | 33 |

Example 9

Figure 6:
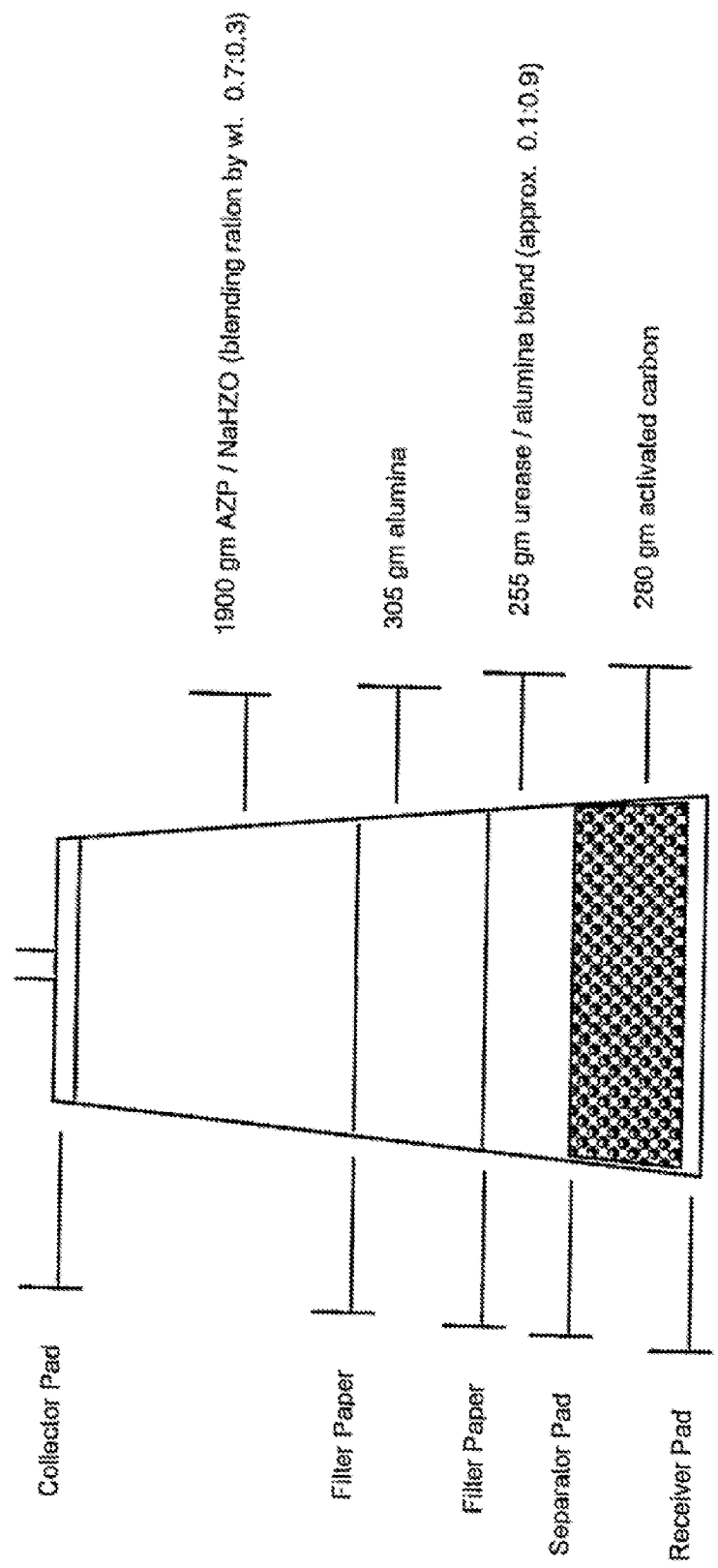
FIG. 6 is a schematic diagram of a sorbent cartridge according to various embodiments.

Test in Example 8 was repeated but by the cartridge with a configuration as shown in FIG. 6. The time variation of regenerated dialysate composition before and after NaHCO$_3$ infusion is shown in TABLE 7 and TABLE 8.

TABLE 7

Dialysate composition data in the cartridge effluent after CO$_2$ degassing but before NaHCO$_3$ re-infusion at Location ①

| | Time (min) | | | | | | | | |
|---|---|---|---|---|---|---|---|---|---|
| | 0 | 10 | 20 | 30 | 45 | 60 | 90 | 120 | 150 |
| NH$_4^+$—N | 0 | 0 | 0 | 0 | 0 | 0 | 0 | 0 | 1.05 |
| pH | 6.76 | 2.70 | 2.53 | 2.50 | 2.51 | 2.53 | 2.50 | 2.51 | 2.50 |
| Na$^+$ (mEq/L) | 115 | 114 | 115 | 114 | 115 | 115 | 114 | 114 | 115 |
| HCO$_3^-$ (mEq/L) | 0 | 0 | 0 | 0 | 0 | 0 | 0 | 0 | 0 |
| Cl$^-$ (mEq/L) | 105 | 106 | 104 | 105 | 104 | 106 | 105 | 105 | 104 |
| Ca$^{2+}$ (mEq/L) | <0.2 | <0.2 | <0.2 | <0.2 | <0.2 | <0.2 | <0.2 | <0.2 | <0.2 |
| K$^+$ (mEq/L) | <0.2 | <0.2 | <0.2 | <0.2 | <0.2 | <0.2 | <0.2 | <0.2 | <0.2 |
| Mg$^{2+}$ (mEq/L) | <0.1 | <0.1 | <0.1 | <0.1 | <0.1 | <0.1 | <0.1 | <0.1 | <0.1 |
| BUN (mg/dL) | 0 | 0 | 0 | 0 | 0 | 0 | 0 | 0 | 0.1 |
| Creatinine (mg/dL) | <0.2 | <0.2 | <0.2 | <0.2 | <0.2 | <0.2 | <0.2 | <0.2 | <0.2 |
| PO$_4$–P (mg/dL) | 0.04 | 0.03 | 0.01 | 0.05 | 0.07 | 0.08 | 0.06 | 0.07 | 0.05 |

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skill in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A sorbent cartridge comprising a layer of a mixture of acid zirconium phosphate (AZP) and alkaline hydrous zirconium oxide (NaHZO) in the sorbent cartridge, and wherein said acid zirconium phosphate is the only form of zirconium phosphate present in said layer.

2. The sorbent cartridge of claim 1, wherein the cartridge comprises at least two layers, wherein at least one of the layers comprises the combination of AZP and NaHZO.

3. The sorbent cartridge of claim 1, wherein the AZP and the NaHZO comprise particles having an average grain size of from about 25 microns to about 60 microns.

4. The sorbent cartridge of claim 1, wherein the combination has a pH of from about 3 to about 7.

5. The sorbent cartridge of claim 1, wherein the combination has a pH of from about 3.5 to about 4.

6. The sorbent cartridge of claim 1, wherein the combination has a pH of from about 5.5 to about 6.

7. The sorbent cartridge of claim 1, wherein the AZP and NaHZO are each present in the combination in an amount to produce an NaHZO:AZP weight ratio of from about 0.2:0.8 to about 0.8:0.2.

8. The sorbent cartridge of claim 7, wherein the NaHZO:AZP weight ratio is from about 0.5:0.5 to about 0.6:0.4.

9. The sorbent cartridge of claim 7, wherein the NaHZO:AZP weight ratio is about 0.4:0.6.

10. The sorbent cartridge of claim 7, wherein the NaHZO:AZP weight ratio is from about 0.22:0.78 to about 0.33:0.67.

11. The sorbent cartridge of claim 1, further comprising zirconium phosphate (ZrP) as an additional layer in the sorbent cartridge.

12. The sorbent cartridge of claim 11, wherein the ZrP has a pH of from about 3 to about 7.

13. The sorbent cartridge of claim 11, wherein the ZrP has a pH of from about 3.5 to about 4.

14. The sorbent cartridge of claim 11, wherein the ZrP has a pH of from about 5.5 to about 6.

15. The sorbent cartridge of claim 1, further comprising activated carbon, immobilized urease, or combinations thereof.

16. The sorbent cartridge of claim 15, wherein the activated carbon and the immobilized urease are each present as a layer in the sorbent cartridge.

17. The sorbent cartridge of claim 1, wherein the sorbent cartridge is configured to restore the balance of $Na^-$ and $HCO_3^-$ in spent dialysate to levels found in fresh dialysate.

18. A method to regenerate or purify spent dialysate comprising passing the spent dialysate through the sorbent cartridge of claim 1.

19. A method to regenerate or purify spent dialysate comprising passing the spent dialysate through the sorbent cartridge of claim 11.

20. The method of claim 18, wherein the method comprises restoring the spent dialysate to original balance of $Na^+$ and $HCO_3^-$ contents found in fresh dialysate.

21. The method of claim 18, wherein the method comprises restoring the spent dialysate to original pH of fresh dialysate.

22. The method of claim 18, wherein the regenerated dialysate has a pH from about 6.8 to about 7.4.

23. The method of claim 18, wherein the regenerated dialysate has a $Na^-$ content from about 110 mEq/L to about 150 mEq/L.

24. The method of claim 18, wherein the regenerated dialysate has a $HCO_3^-$ content from about 25 mEq/L to about 35 mEq/L.

25. The method of claim 18, wherein the dialysate is regenerated without generating $CO_2$ gas bubbles.

26. The method of claim 18, wherein the dialysate is regenerated without releasing $Na^+$ to the dialysate.

27. The method of claim 18, wherein $NaHCO_3$ present in spent dialysate is converted by the AZP to form carbonic acid and $CO_2$, and the carbonic acid and the $CO_2$, are converted by the NaHZO to form $NaHCO_3$.

28. A method of preparing purified fresh dialysate for dialysis comprising passing the dialysate through the sorbent cartridge of claim 1.

29. The method of claim 28, wherein the dialysate comprises tap water.

* * * * *